United States Patent
Webster et al.

[19]

[11] Patent Number: 6,096,073
[45] Date of Patent: Aug. 1, 2000

[54] METHOD OF DEPLOYING A STENT AT A LESION SITE LOCATED AT A BIFURCATION IN A PARENT VESSEL

[75] Inventors: Mark Webster, Auckland, New Zealand; H. Elizabeth Noll, Del Mark, Calif.

[73] Assignee: SciMed Life Systems, Inc., Maple Grove, Minn.

[21] Appl. No.: 09/028,792

[22] Filed: Feb. 24, 1998

[51] Int. Cl.[7] ................................................ A61F 2/06
[52] U.S. Cl. ......................................................... 623/1.16
[58] Field of Search .......................... 623/1.1, 1.2, 1.16, 623/1, 12

[56] References Cited

U.S. PATENT DOCUMENTS

| | | | |
|---|---|---|---|
| 4,730,616 | 3/1988 | Frisbie et al. | 128/348 |
| 4,896,670 | 1/1990 | Crittenden | 606/194 |
| 4,994,071 | 2/1991 | MacGregor | 606/194 |
| 5,143,093 | 9/1992 | Sahota | 128/898 |
| 5,219,355 | 6/1993 | Parodi et al. | 606/191 |
| 5,316,023 | 5/1994 | Palmaz et al. | 128/898 |
| 5,413,581 | 5/1995 | Goy | 606/194 |
| 5,591,228 | 1/1997 | Edoga | 623/1 |
| 5,607,444 | 3/1997 | Lam | 606/194 |
| 5,609,627 | 3/1997 | Goiciechea et al. | 623/1 |
| 5,613,980 | 3/1997 | Chauhan | 606/194 |
| 5,617,878 | 4/1997 | Taheri | 128/898 |
| 5,632,762 | 5/1997 | Myler | 606/194 |
| 5,632,763 | 5/1997 | Glastra | 606/194 |
| 5,639,278 | 6/1997 | Dereume et al. | 623/1 |
| 5,643,340 | 7/1997 | Nunokawa | 623/1 |
| 5,669,924 | 9/1997 | Shaknovich | 606/108 |
| 5,720,735 | 2/1998 | Dorros | 604/284 |
| 5,749,825 | 5/1998 | Fischell et al. | 600/3 |
| 5,749,890 | 5/1998 | Shaknovich | 606/198 |
| 5,755,734 | 5/1998 | Richter et al. | 606/194 |
| 5,755,735 | 5/1998 | Richter et al. | 606/194 |
| 5,755,770 | 5/1998 | Ravenscroft | 623/1 |
| 5,755,771 | 5/1998 | Penn et al. | 623/1 |
| 5,755,772 | 5/1998 | Evans et al. | 623/1 |
| 5,755,773 | 5/1998 | Evans et al. | 623/1 |
| 5,755,778 | 5/1998 | Kleshinski | 623/1 |
| 5,776,101 | 7/1998 | Goy | 604/104 |
| 5,782,906 | 7/1998 | Marshall et al. | 623/1 |
| 5,800,518 | 9/1998 | Piplani et al. | . |
| 5,824,055 | 10/1998 | Spiridigliozzi et al. | . |
| 5,868,777 | 2/1999 | Lam | 606/194 |
| 6,033,434 | 3/2000 | Borghi | 623/1 |

FOREIGN PATENT DOCUMENTS

| | | |
|---|---|---|
| 0 479 730 B1 | 4/1992 | European Pat. Off. . |
| 2 678 508-A1 | 1/1993 | European Pat. Off. . |
| 0 686 379 A2 | 12/1995 | European Pat. Off. . |
| WO 95/21592 | 8/1995 | WIPO . |
| WO 96/34580 | 11/1996 | WIPO . |
| WO 96/41592 | 12/1996 | WIPO . |
| WO 97/07752 | 3/1997 | WIPO . |
| WO 97/15346 | 5/1997 | WIPO . |
| WO 97/41803 | 11/1997 | WIPO . |
| WO 98/19628 | 5/1998 | WIPO . |
| WO 99/03462 | 1/1999 | WIPO . |
| WO 99/04726 | 2/1999 | WIPO . |

*Primary Examiner*—Jeffrey A. Smith
*Attorney, Agent, or Firm*—D. Peter Hochberg; William H. Holt

[57] ABSTRACT

A system and method are provided for dilatation of, and delivery and deployment of stents at, a bifurcation. The system includes two guidewires, one disposed in each branch of the bifurcation. A device and stents are provided which allow accurate dilatation and stenting of the bifurcation, without removing the guidewires, and such that the stents closely conform to the geometry of the bifurcation.

9 Claims, 8 Drawing Sheets

METHOD OF DEPLOYING A STENT AT A LESION SITE LOCATED AT A BIFURCATION IN A PARENT VESSEL

BACKGROUND OF THE INVENTION

The present invention relates to a system for treating vascular disease. More specifically, the present invention relates to a system for performing dilatation and for deploying a stent in a bifurcation lesion.

Vascular disease currently represents a prevalent medical condition. Typical vascular disease involves the development of a stenosis in the vasculature. The particular vessel containing the stenosis can be completely blocked (or occluded) or it can simply be narrowed (or restricted). In either case, restriction of the vessel caused by the stenotic lesion results in many well known problems caused by the reduction or cessation of blood circulation through the restricted vessel.

A bifurcation is an area of the vasculature where a first (or parent) vessel is bifurcated into two or more branch vessels. It is not uncommon for stenotic lesions to form in such bifurcations. The stenotic lesions can affect only one of the vessels (i.e., either of the branch vessels or the parent vessel) two of the vessels, or all three vessels.

Vascular stents are also currently well known. Vascular stents typically involve a tubular stent which is movable from a collapsed, low profile, delivery position to an expanded, deployed position. The stent is typically delivered using a stent delivery device, such as a stent delivery catheter. In one common technique, the stent is crimped down to its delivery position over an expandable element, such as a stent deployment balloon. The stent is then advanced using the catheter attached to the stent deployment balloon to the lesion site under any suitable, commonly known visualization technique. The balloon is then expanded to drive the stent from its delivery position to its deployed position in which the outer periphery of the stent frictionally engages the inner periphery of the lumen. In some instances, the lumen is predilated using a conventional dilatation catheter, and then the stent is deployed to maintain the vessel in an unoccluded, and unrestricted position.

While there have recently been considerable advances in stent design and stent deployment techniques, there is currently no adequate method of treating bifurcation lesions, particularly where both downstream branch vessels are affected by the lesion. Current techniques of dealing with such lesions typically require the deployment of a slotted tube stent across the bifurcation. However, this compromises the ostium of the unstented branch.

Further, once the first stent is deployed, the treating physician must then advance a dilatation balloon between the struts of the stent already deployed in order to dilate the second branch vessel. The physician may then attempt to maneuver a second stent through the struts of the stent already deployed, into the second branch vessel for deployment. This presents significant difficulties. For example, dilating between the struts of the stent already deployed tends to distort that stent. Further, deploying the second stent through the struts of the first stent is not only difficult, but it can also distort the first stent.

In addition, the current systems used to deploy stents in a bifurcated lesion have other significant disadvantages. For example, such techniques typically involve the advancement of a guidewire past the bifurcation lesion, and into a first of the branch vessels. That guidewire is then used to advance the predilitation device to dilate the vessel, and then to advance the stent deployment device to deploy the stent in the parent vessel and in the first branch vessel. Then, the guidewire must be withdrawn from the first branch vessel and then maneuvered and advanced through the structure of the first stent and into the second branch vessel. The guidewire is then used for guiding advancement of the dilatation device into the second branch vessel, and for guiding advancement of the stent deployment device into the second branch vessel for deployment of the second stent.

Also, there are currently no stents having shapes which closely conform to the geometry of a typical bifurcation. Thus, the deployment of a conventional stent in a bifurcation lesion either leaves one of the branch stents impinging on the ostium of the other branch, or leaves a significant portion of the vessel wall in the area of the bifurcation unstented.

SUMMARY OF THE INVENTION

A system and method are provided for dilatation of, and for delivery and deployment of stents at, a bifurcation. The system includes two guidewires, one disposed in each branch of the bifurcation. A device and stents are provided which allow accurate dilatation and stenting of the bifurcation, without removing the guidewires, and such that the stents closely conform to the geometry of the bifurcation.

DETAILED DESCRIPTION OF THE PREFERRED EMBODIMENTS

Figure 1:
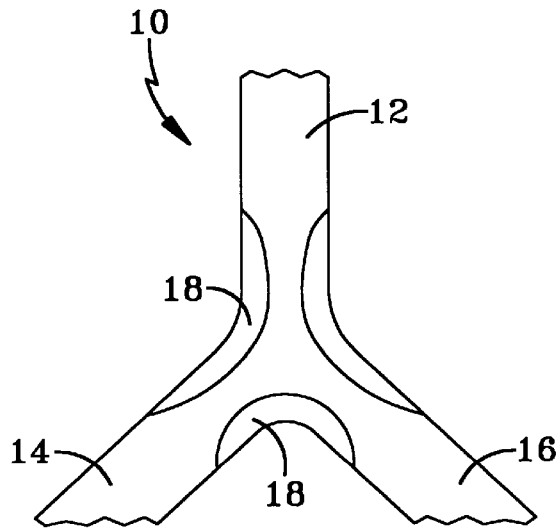
FIG. 1 illustrates a typical bifurcation lesion.

FIG. 1 illustrates a bifurcation 10 which includes parent vessel 12, first branch vessel 14 and second branch vessel 16. FIG. 1 also illustrates that a bifurcation lesion 18 has developed in bifurcation 10. Lesion 18 illustrates one common bifurcation lesion in that it extends up into parent vessel 12 and down into both branch vessels 14 and 16.

In order to treat bifurcation lesion 18, it is commonly first dilated with a conventional angioplasty balloon catheter dilatation device. Conventional treatment of bifurcation lesions, such as lesion 18, also includes stenting the vessels containing lesion 18.

Figure 2:
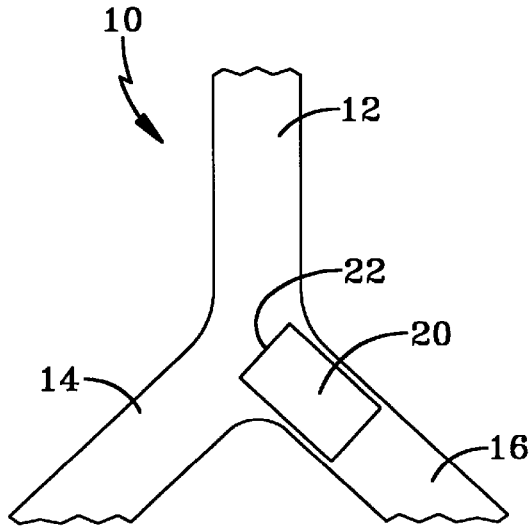
FIG. 2 illustrates the deployment of a conventional stent in a bifurcation lesion in accordance with the prior art.

FIG. 2 illustrates one prior art method of stenting bifurcation lesion 18. FIG. 2 illustrates that, in accordance with one prior art technique, a conventional stent 20 is deployed in the branching vessels 14 or 16. However, conventional stent 20 is not configured to conform to the geometry of bifurcation 10. Thus, end 22 of stent 20 protrudes into parent vessel 12, and impinges on the ostium of branch vessel 14.

Figure 3:
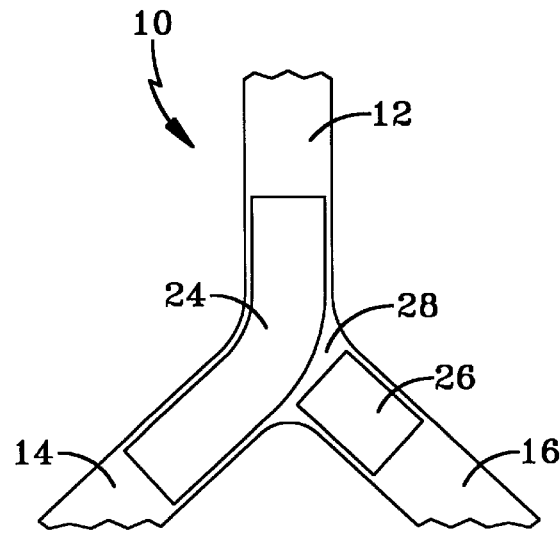
FIG. 3 illustrates the deployment of another stent in a bifurcation lesion in accordance with the prior art.

FIG. 3 illustrates another prior art method of stenting a bifurcation lesion. In FIG. 3, a first stent 24 is deployed in parent vessel 12 and a first branch 14. A guidewire is typically advanced into branch vessel 14, and then a stent delivery apparatus is advanced over the guidewire to deploy stent 24. Next, the guidewire is removed from vessel 14 and advanced through the structure of stent 24 and into branch vessel 16. A second stent 26 is delivered, in a collapsed, delivery position, over the guidewire. The physician attempts to manipulate stent 26 through the structure of stent 24, and into branch vessel 16. The stent is then deployed in vessel 16.

However, the structure of stent 24 obscures the ostium of vessel 16. Also, dilatation of lesion 18 in vessel 16, when done through the structure of stent 24, can distort the structure of stent 24. Further, not only is it difficult to maneuver the stent deployment device through the structure of 24, but simply the act of deploying stent 26 through the structure of stent 24 can also tend to distort the structure of stent 24.

It should also be noted that stents 24 and 26 are shaped as conventional stents. Thus, they are not shaped to conform closely to the geometry of bifurcation 10. This leaves a significant portion 28 of the vessel wall in the area of bifurcation 10 unstented.

Figure 4:
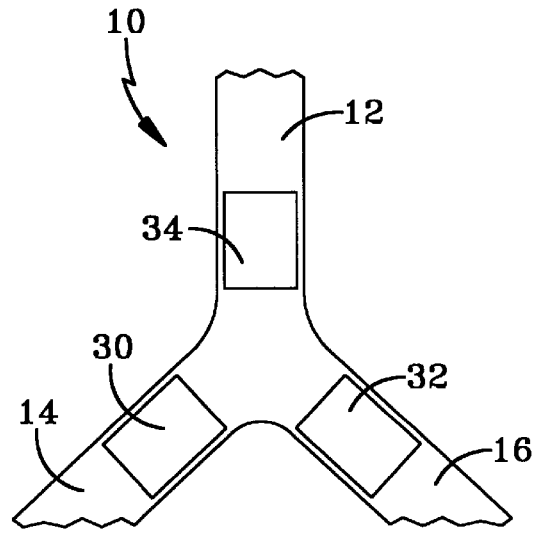
FIG. 4 illustrates yet another prior art method of stenting a bifurcation lesion.

FIG. 4 illustrates yet another prior art method of deploying stents in a bifurcation lesion. FIG. 4 illustrates that three conventional stents 30, 32 and 34 are deployed in branch vessels 14 and 16, and in parent vessel 12. In order to deploy stents 30, 32 and 34, a guidewire is first advanced into branch vessel 14, and vessel 14 is dilated. The stent deployment apparatus is then advanced over the guidewire to deploy stent 30 in vessel 14. The guidewire is then withdrawn and manipulated such that it can be advanced through branch vessel 16, at which point branch vessel 16 is dilated. The stent deployment apparatus is then advanced into branch vessel 16 to deploy stent 32. Finally, the stent deployment apparatus is positioned in a parent vessel 12 which is dilated, and stent 34 is deployed. However, as with the techniques illustrated in FIGS. 2 and 3, the technique illustrated in FIG. 4 involves the delivery of stents having conventional geometries which do not closely conform to the geometry of bifurcation 10. As FIG. 4 illustrates, this also leaves significant portions of the vessel wall in the area of bifurcation 10 unstented.

Figure 5:
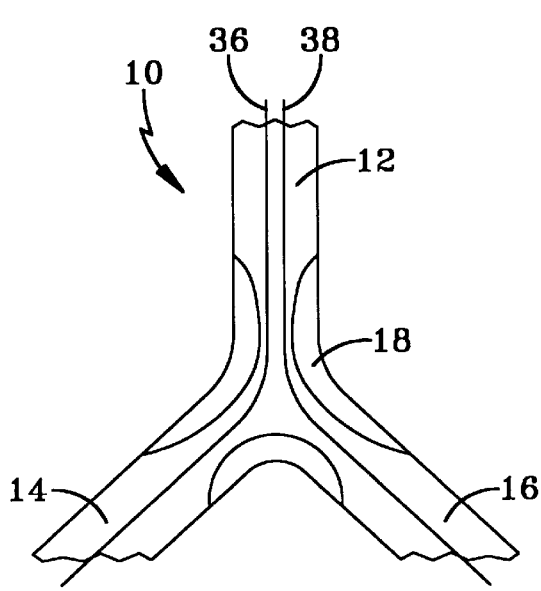
FIGS. 5–7 illustrate a method of dilating a bifurcation lesion in accordance with one aspect of the present invention.
Figure 6:
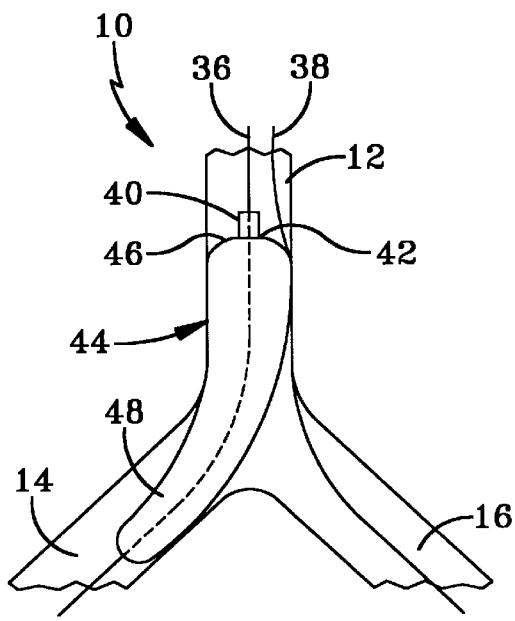
Figure 7:
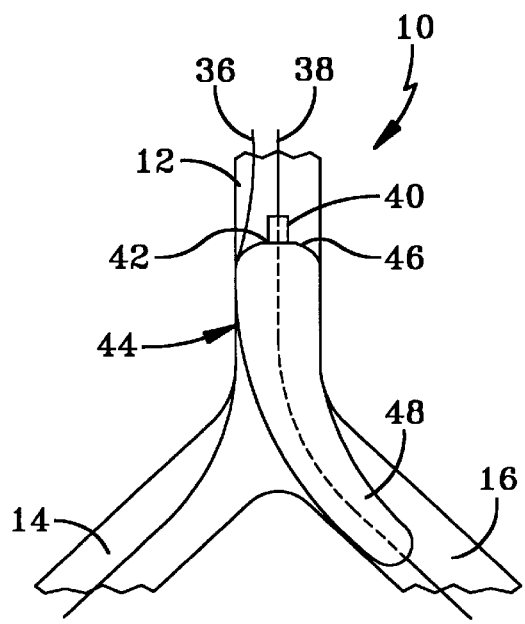

FIGS. 5–7 illustrate a technique for dilating a bifurcation lesion in accordance with one aspect of the present invention. Another device and technique are illustrated later in the specification with respect to FIGS. 12A–12C. However, FIG. 5 illustrates that a pair of guidewires 36 and 38 are first advanced through parent vessel 12, and into branch vessels 14 and 16. Guidewires 36 and 38 are preferably any suitable and conventional guidewires, and are introduced through a guide catheter which is placed in the vasculature in a conventional manner, such as through a femoral artery. However, other suitable techniques for deploying guidewires 36 and 38 in the positions illustrated in FIG. 5 can also be used.

FIG. 6 illustrates that, once guidewires 36 and 38 are in position, a dilatation catheter 40 is advanced over one of the guidewires, such as guidewire 36. In a preferred embodiment, catheter 40 includes a conventional elongate balloon catheter shaft 42 having an inflation lumen and a guidewire lumen therein and supporting a dilatation balloon 44. In one preferred embodiment, dilatation balloon 44 has a proximal end 46 and a distal end 48. Proximal end 46 preferably has a larger outer diameter, in the inflated position, than distal end 48. This is preferred because, in typical bifurcations, the parent vessel 12 has a larger inner diameter than either of the branch vessels 14 or 16. Catheter 40 is advanced over guidewire 36 until the distal end 48 of balloon 44 is in an appropriate position in branching vessel 14, and so that proximal end 46 of balloon 44 is suitably located in parent vessel 12. Balloon 44 is then expanded in a known manner to accomplish dilatation. In the preferred embodiment, dilatation of branch vessel 14 is accomplished while leaving guidewire 38, which has a distal end positioned in branch vessel 16, in place.

FIG. 7 illustrates that catheter 40 is withdrawn after dilating branch vessel 14, and catheter 40 (or another catheter) is advanced over guidewire 38. Catheter 40 is advanced to a position similar to that shown in FIG. 6, except that distal end 48 of balloon 44 is suitably located in branch vessel 16. Balloon 44 is then inflated, in a known manner, in order to accomplish dilatation of branch vessel 16. After dilatation is complete, dilatation catheter 40 is removed from the vasculature.

Figure 8A:
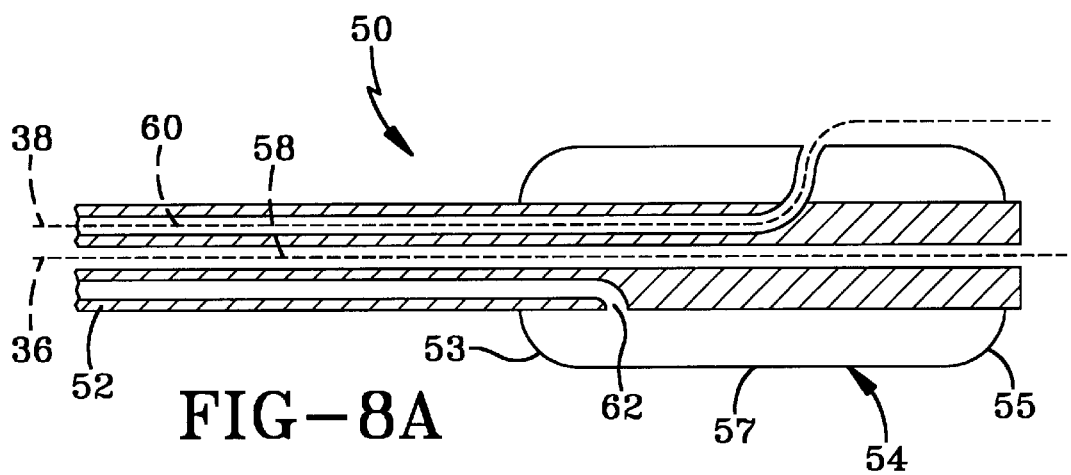
FIGS. 8A and 8B illustrate first and second embodiments, respectively, of a stent delivery catheter in accordance with one aspect of the present invention.

FIG. 8A illustrates one embodiment of a dilatation and stent deployment device 50 in accordance with one aspect of the present invention. Device 50 is illustrated as an over-the-wire catheter. Stent deployment device 50 includes a catheter shaft 52 and a stent deployment balloon 54. Balloon 54 includes proximal end 53, distal end 55 and intermediate portion 57. Shaft 52 includes an inflation lumen 56, a first guidewire lumen 58 and the second guidewire lumen 60. Inflation lumen 56 is preferably in fluid communication with the interior of balloon 54 through aperture 62. A proximal end of catheter shaft 52 is thus preferably couplable to a source of fluid pressure for delivering fluid under pressure to, and withdrawing fluid from, the interior of balloon 54.

First guidewire lumen 58 is preferably configured as a conventional guidewire lumen which extends from the proximal end of catheter shaft 52 through the distal end of catheter shaft 52 (distal of balloon 54) such that catheter shaft 52 can be advanced over guidewire 36 or 38 in a conventional manner.

In the embodiment shown in FIG. 8A, second guidewire lumen 60 also extends from the proximal end of catheter shaft 52 to a distal region of catheter shaft 52, but not all the way to the distal tip of shaft 52. Rather, the distal ostium of guidewire lumen 60 is disposed in intermediate region 57 of balloon 54. Thus, guidewire 36 or 38 (38 illustrated in the illustration of FIG. 8A) exits the distal ostium of guidewire lumen 60 through the intermediate portion 57 of balloon 54.

The operation of device 50 is described in greater detail later in the specification. Briefly, however, a stent is first crimped over balloon 54 in a low profile, delivery position. The distal end of device 50 is then advanced to an appropriate position for deployment of the stent, and balloon 54 is inflated by introducing fluid under pressure into the interior of balloon 54 through inflation lumen 56. Balloon 54 is then deflated and device 50 can then by removed.

Figure 8B:
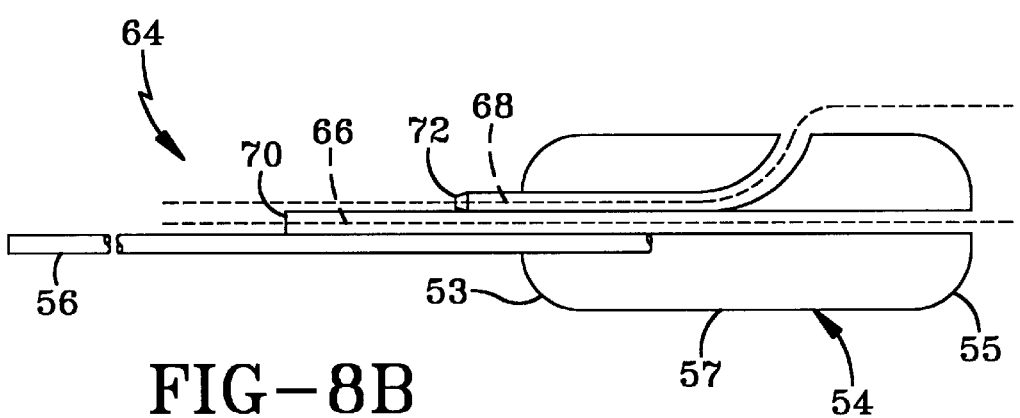

FIG. 8B is a simplified diagram of a second embodiment of a dilation and stent delivery device 64. Device 64 is similar to device 50, shown in FIG. 8B, and similar items are similarly numbered. However, device 64 is arranged in a monorail configuration such that inflation lumen 56 is the only lumen which extends to the proximal end of the catheter shaft 52. Device 64 is provided with first guidewire lumen 66 and second guidewire lumen 68 which have proximal ostiums 70 and 72, respectively, which are disposed just proximally of the proximal end 53 of balloon 54. The remainder of the construction of device 64, and the operation of device 64, is similar to that described with respect to device 50 shown in FIG. 8A.

Balloon 54 is preferably made of a non-compliant material. This enables it to be used for both stent deployment and post deployment high pressure inflation. The inflated diameter of the proximal end 53 of balloon 54 is preferably approximately 0.5 mm larger than the inflated diameter of distal end 55 of balloon 54. Further, in one preferred embodiment, balloon 54 is preferably approximately 22–24 mm in length from its distal end 53 to its proximal end 55.

Figure 9A:
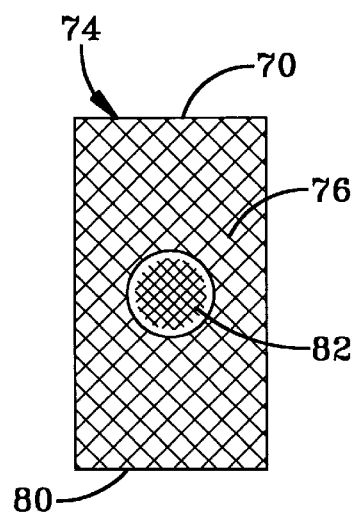
FIGS. 9A–9E illustrate embodiments of stents used in accordance with other aspects of the present invention.

FIGS. 9A–9E illustrate a plurality of stents used in accordance with one aspect of the present invention. FIG. 9A illustrates one embodiment of a stent 74 for use with one of devices 50 or 64. Stent 74 is conventional in many respects. For example, stent 74 may be a commercially available NIR stent, or a Palmaz-Schatz stent. Thus, stent 74 is formed of a tubular structural wall 76 having a first end 78 and a second end 80. During insertion, stent 74 is collapsed to a low profile position and is positioned coaxially within any desired lumen. Then, stent 74 is expanded radially outwardly such that structural wall 76 frictionally engages the interior of the lumen in which stent 74 is deployed. However, stent 74 also has a central aperture 82 formed therein. Aperture 82 is simply a single hole in tubular wall structure 76. Aperture 82 is preferably formed at or near a central region of stent 74 between its first end 78 and second end 80.

Figure 9E:
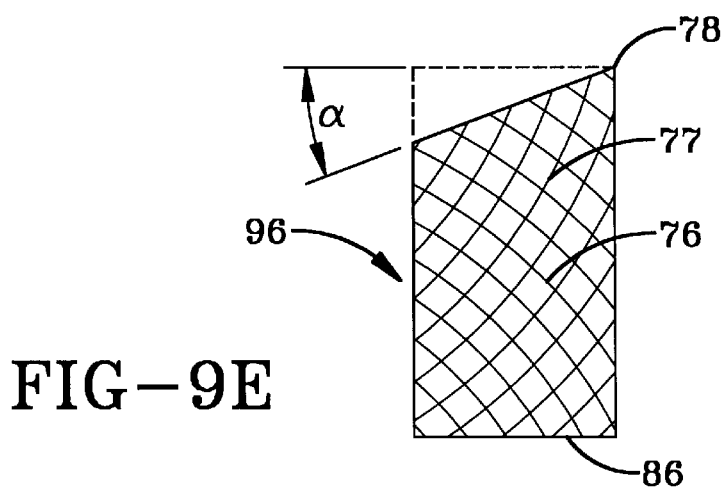
Figure 9B:
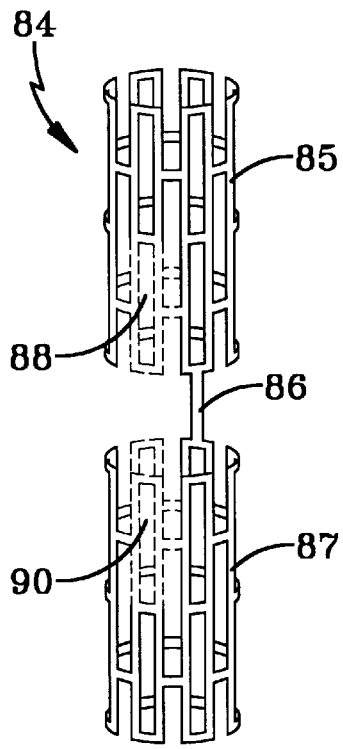
Figure 9C:
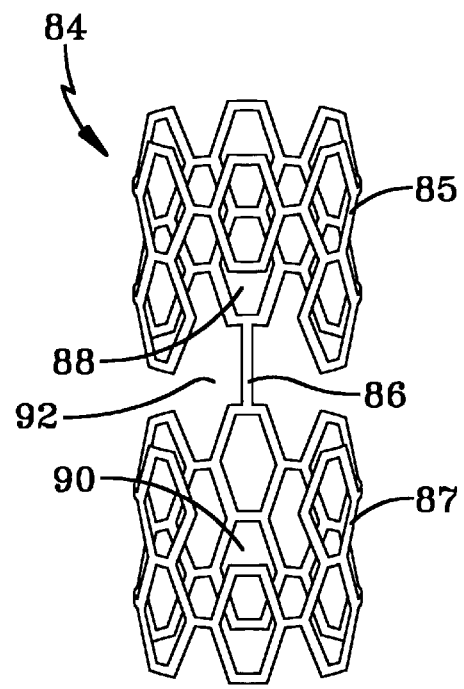

FIG. 9B illustrates a second embodiment of a stent 84 in accordance with one aspect of the present invention. Stent 84 is illustrated in the collapsed position and is preferably formed of two commercially available Palmaz-Schatz stents 85 and 87 connected by connecting element 86. In addition, stents 85 and 87 have a portion of the structure removed to form apertures 88 and 90. Apertures 88 and 90 essentially serve the same purpose as aperture 82 in stent 74, and this will be described in greater detail later in the specification. FIG. 9C illustrates stent 84 in an expanded, deployed position.

Figure 9D:
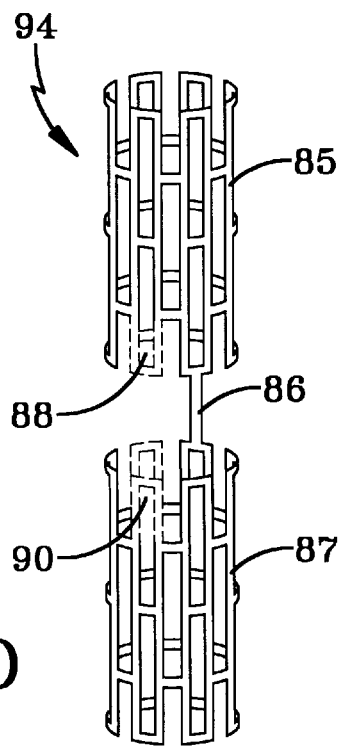

FIG. 9D illustrates another embodiment of a stent 94 in accordance with one aspect of the present invention. Stent 94 is similar to stent 84 and similar items are similarly numbered. The only difference between stent 94 and stent 84 is that stent 94 has less of the stent structure removed in areas 88 and 90. This provides a smaller aperture in the center of the deployed stent.

FIG. 9E illustrates another stent 96 in accordance with one aspect of the present invention. Stent 96 is similar to stent 74 shown in FIG. 9A, and similar items are similarly numbered. However, stent 96 has no central aperture 82 therein. Rather, the tubular wall structure 76 of stent 96 is intact substantially throughout the entire length of the stent 96. However, stent 96 has a portion of first end 78 removed therefrom. This causes first end 78 to be disposed at an angle relative to a longitudinal axis 97 of stent 96. As will be described later in the specification, stent 96 is used, in one preferred embodiment, as the second stent deployed in one of the branching vessels after a first stent, such as stent 74, is deployed in a first branching vessel and in the parent vessel. The first end 78 of stent 96 is disposed at an angle to more closely conform to the bifurcation to leave less of the vessel wall in the region of the bifurcation unstented.

Most bifurcations have branching vessels which extend at an angle less than 90° relative to one another. In fact, many bifurcations where stenting is required have branching vessels which extend in a range of approximately 30°–70° relative to one another. Therefore, first end 78 of stent 95 is cut at an angle $\alpha$ which is preferably in a range of approximately 30°–70°, and more preferably in a range of approximately 45°–60°.

FIGS. 10A–10D illustrate deployment of stents, such as stents 74 and 96, within bifurcation 10. Prior to insertion of the stents or the stent deployment device into the vasculature, the bifurcation lesion is preferably dilated as discussed with respect to FIGS. 5–7. Then, a stent deployment apparatus, such as device 50 shown in FIG. 8A, is placed on guidewires 36 and 38 as shown in FIG. 8A. Guidewire 36 extends through guidewire lumen 58, from a proximal end of catheter shaft 52 out through the distal end of catheter shaft 52. Guidewire 38 extends within guidewire lumen 60, through catheter shaft 52, and out through intermediate portion 57 of balloon 54. Also, a stent, such as stent 74, is placed over balloon 54. Aperture 82 is aligned with the ostium of guidewire 60 which is disposed on the outer surface of balloon 54. Thus, guidewire 38 exits guidewire lumen 60 through the intermediate portion 57 of balloon 54 and also exits stent 74 through aperture 82.

Device 50 is then advanced, with stent 74 crimped down over balloon 54 in the insertion position, into the vascular system, such as through a femoral artery. Device 50 is advanced over guidewires 36 and 38 to a region proximate bifurcation 10. Because guidewire 38 exits aperture 82 in stent 74, which is crimped over balloon 54, apparatus 50 will be advanced to a position where end 80 of stent 74 is disposed within branch vessel 14. Also, because guidewire 38 extends into branch vessel 16, as the physician advances device 50 over guidewires 36 and 38, aperture 82 will naturally become aligned with the ostium of branching vessel 16. At that point, balloon 54 is inflated by introducing fluid under pressure through inflation lumen 56. This causes stent 74 to expand to its expanded position. This is illustrated in FIG. 10B.

Figure 10A:
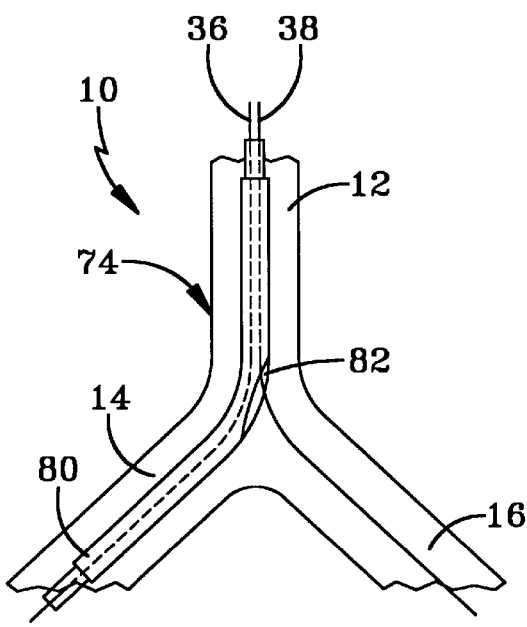
FIGS. 10A–10D illustrate the deployment of stents in a bifurcation lesion in accordance with one aspect of the present invention.
Figure 10B:
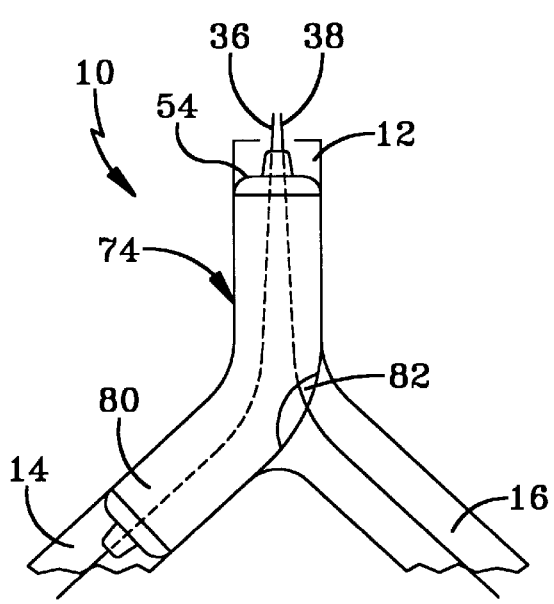
Figure 10C:
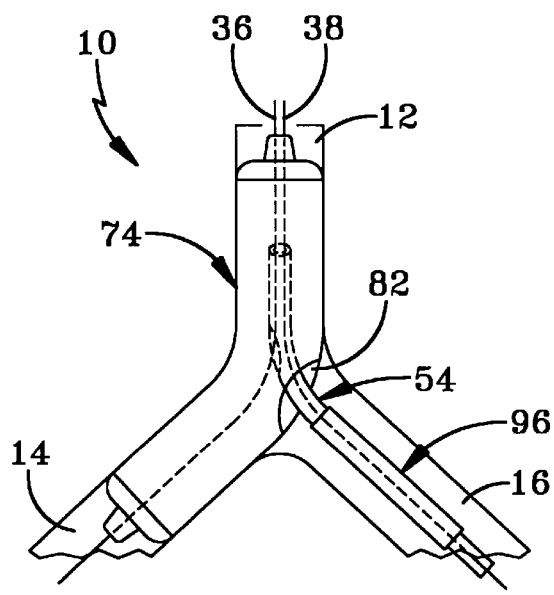

FIG. 10B also illustrates that, in the expanded position, aperture 82, which is preferably just larger than the ostium of branch vessel 16, is closely aligned with the ostium of branch vessel 16 under the guidance of guidewire 38. Once stent 74 is deployed, balloon 54 is deflated such that it no longer frictionally engages stent 74, and device 50 is removed from the vasculature leaving stent 74 in place.

Next, another stent, such as stent 96 shown in FIG. 9E, is assembled onto device 50. Device 50 is then threaded onto guidewires 36 and 38 in the opposite orientation from when deploying stent 74. In other words, stent deployment device 50 is placed on guidewires 36 and 38 such that guidewire 36 is disposed within guidewire lumen 60, and guidewire 38 is disposed within guidewire lumen 58. Also, stent 96 is crimped over the distal end 55 of balloon 54, distal of the ostium of guidewire lumen 60. Stent 96 is preferably arranged such that its longest end is oriented such that it faces proximally on device 50, and such that it is angularly oriented on balloon 54 directly opposite of the ostium of guidewire lumen 60.

Once stent 96 is oriented in this manner, device 50 is then advanced through the vasculature to bifurcation 10. Since, this time, guidewire 36 is exiting through the ostium in balloon 54, device 50 is advanced to the position shown in FIG. 10C, where the distal end 55 of balloon 54 resides within branch vessel 16, and the proximal end resides within parent vessel 12. Also, under the influence of the guidewires 36 and 38, device 50 will be oriented such that the ostium of guidewire lumen 60 is directed toward branch vessel 14. Since stent 96 is disposed only on the distal end 55 of balloon 54, distal of the ostium of the lumen 60, stent 94 will reside substantially entirely within branch vessel 16, but closely proximate the aperture 82 in stent 74.

Figure 10D:
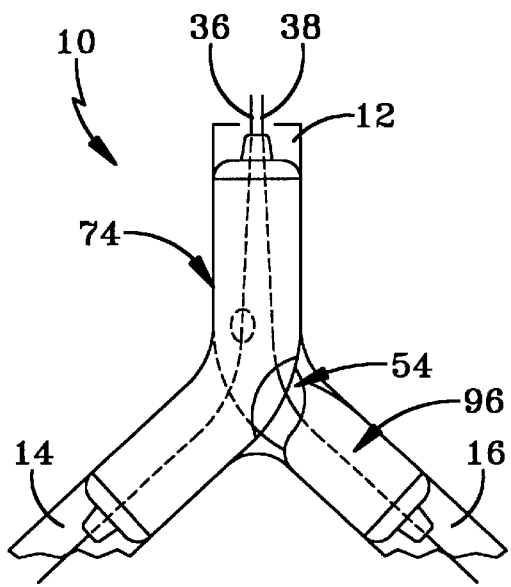

Next, balloon 54 is inflated to drive stent 96 to its radially expanded, deployed position. This is indicated in FIG. 10D. It should be noted that the longest end 77 of stent 96 is oriented such that it faces in the proximal direction, and such that it is angularly opposite the ostium of guidewire lumen 62 on balloon 54. This results in both stents 74 and 96 closely conforming to the geometry of bifurcation 10, leaving very little of the vessel walls in the region of bifurcation 10 unstented.

In another preferred embodiment, two stents such as stent 74 are used instead of stent 96. In that embodiment, a first stent 74 is deployed as illustrated in FIG. 10B. The second stent 74 is then advanced, in the collapsed position, through the deployed stent such that the distal end 80 of the second stent protrudes through aperture 82 in the first stent and into branch vessel 16. The aperture 82 of the second stent is thus positioned to communicate with branch vessel 14. The second stent is then deployed such that nested stent portions are deployed in parent vessel 12 and one distal portion 80 of each stent is deployed in each branch vessel. This eliminates any gaps in the stents at bifurcation 10 and greatly reduces the likelihood that restenosis will occur in that region.

Once the stents are deployed, balloon 54 is deflated and device 50 is removed from the vasculature. If necessary, further dilation can be performed by advancing a standard angioplasty balloon over guidewire 36, guidewire 38, or both (in turn) to within the stent, and inflating it in a standard manner. Guidewires 36 and 38 can then be removed leaving stents 74 and 96 in place. Of course, guidewires 36 and 38 can be removed along with device 50 in a single step.

It should also be noted that device 64 illustrated in FIG. 8B could be used to deploy stents 74 and 96 in a similar fashion as device 50, the difference being that device 64 is of a monorail construction, rather than of a pure over the wire construction.

Figure 11A:
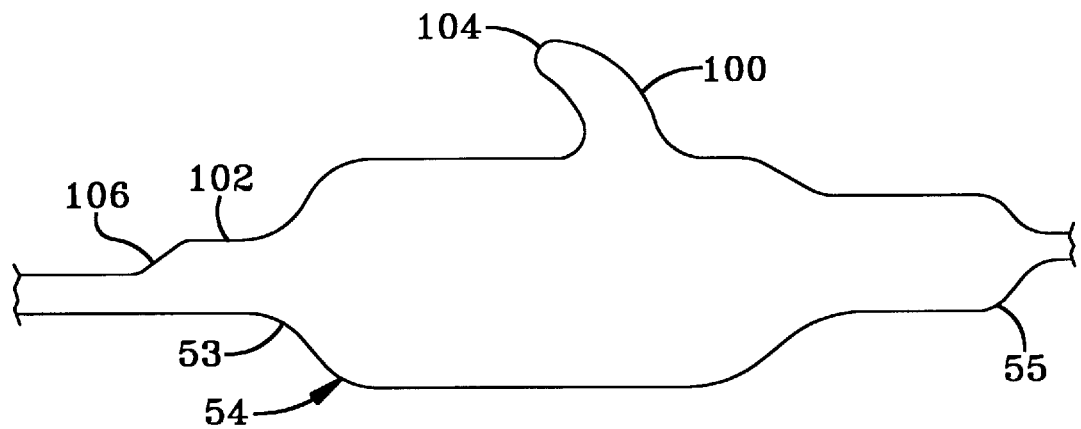
FIGS. 11A–11E illustrate one method of making the stent delivery catheter shown in FIGS. 8A and 8B.
Figure 11B:
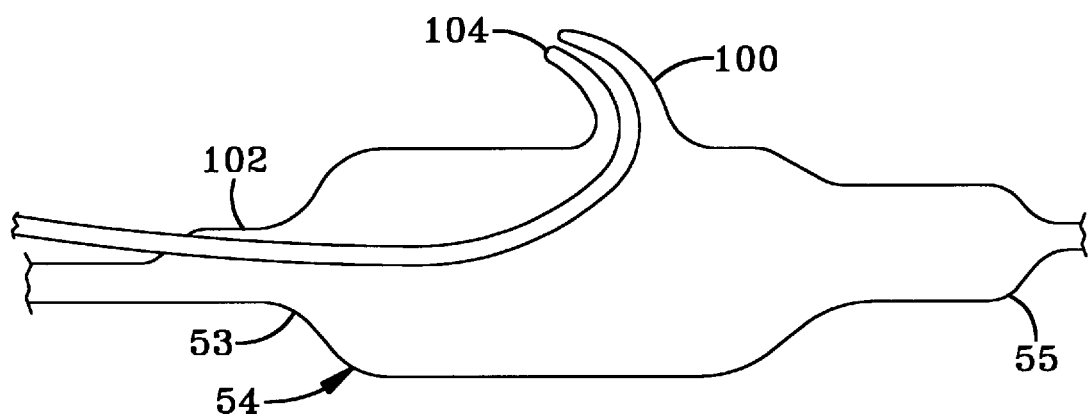

FIGS. 11A–11D illustrate one technique for constructing an apparatus such as device 64. FIG. 11A illustrates that, at a beginning step, a balloon catheter is provided with balloon 54 having a slightly modified shape. The proximal end 53 of balloon 54 is slightly larger than the distal end 55 of balloon 54, in the inflated position. Also, balloon 54 is preferably provided with a protrusion 100 which will eventually be disposed at the site of the ostium of guidewire lumen 60. Further, balloon 54 is provided with an extreme proximal end 102 which is necked down to a much smaller diameter than the proximal portion 53 of balloon 54, in the inflated position.

First, two holes are cut in balloon 54. One is cut in a tip 104 of protrusion 100, and the other is cut in a proximal portion 106 of region 102 of balloon 54. This is illustrated by FIG. 11A.

Next, a guidewire lumen tube, such as a tube 108 formed of polyester or other suitable material is inserted through the hole formed in region 106, and advanced through balloon 54 to the hole formed in tip 104 of protrusion 100. Then, tube 108 the distal end of the tube 108 is welded to the molded balloon material at tip 104.

Figure 11C:
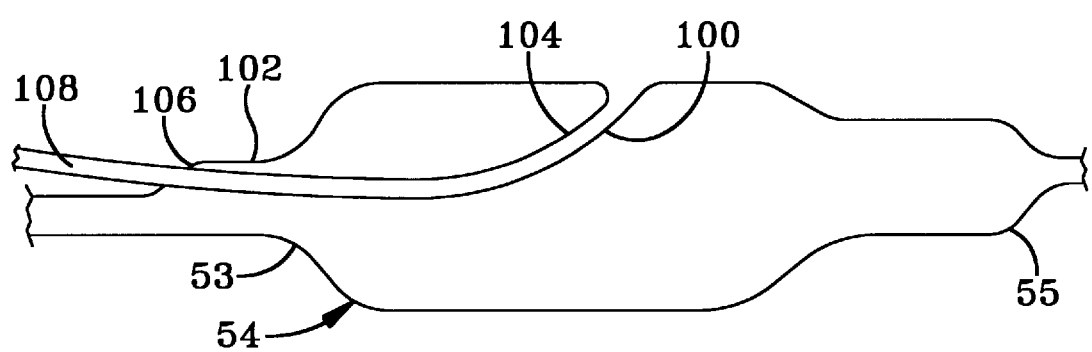

Once tip 104 of balloon 54 is welded to the distal tip of tube 108, tube 108 is withdrawn in the proximal direction as indicted in FIG. 11C. This causes protrusion 100 to invaginate balloon 54 to form the ostium of the guidewire lumen which exits in the intermediate portion 57 of balloon 54.

Figure 11D:
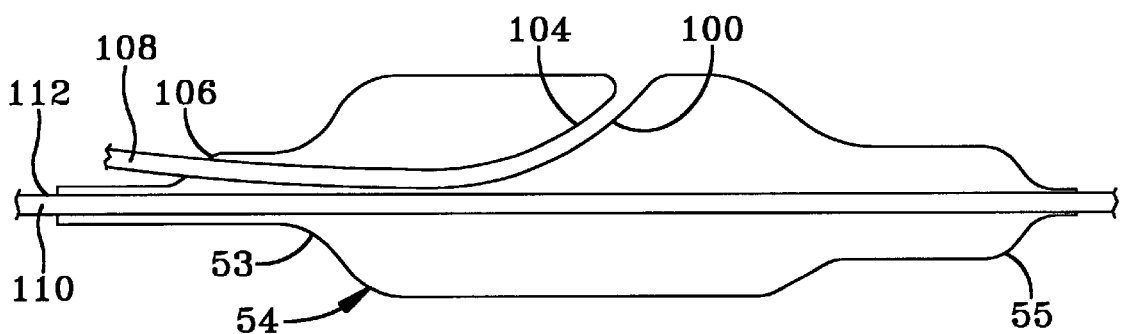

A second guidewire lumen tube 110 is then inserted through a proximal aperture 112 in balloon 54. Tube 110 is inserted through the entire length of balloon 54 such that it exits the distal end of balloon 54. This is illustrated in FIG. 11D. In one preferred embodiment, the two guidewire lumen tubes 108 and 110 are then welded together through the aperture formed in region 106 of balloon 54. This is an optional step, but assists in maintaining accurate alignment between the lumens through balloon 54.

Figure 11E:
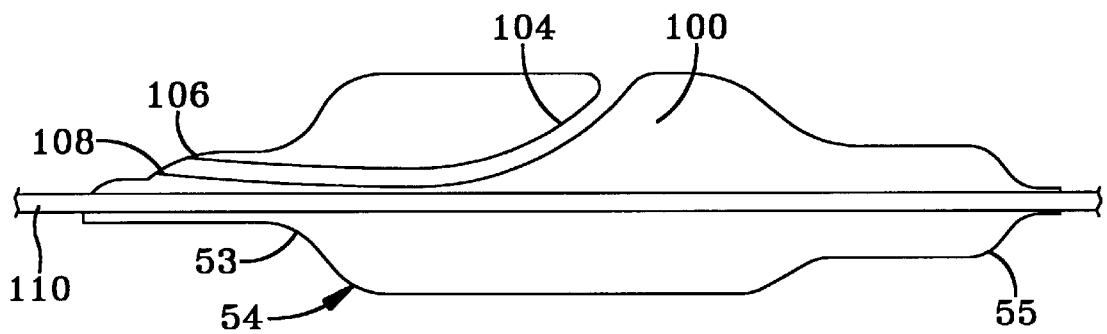

Finally, the proximal portion of lumen tube 108 is cut and the balloon material in region 106 is welded to the cut proximal end of tube 108. In addition, the distal end of balloon 54 is welded to the distal end of tube 110. This is indicated in FIG. 11E.

It should also be noted that, instead of having the second guidewire lumen extend through balloon 54 and exit through the surface of balloon 54, a separate tube can be welded over the surface of the balloon 54, beginning proximal of balloon 54 and extending to somewhere in the intermediate portion 57 of balloon 54. This has one disadvantage in that the deflated profile of the device is larger.

It should also be noted that it may be advantageous, in some instances, to dilate the first stent again, after the second stent has been deployed. This would ensure firm seating of the first stent within the vessel.

Figures 12A, 12B:
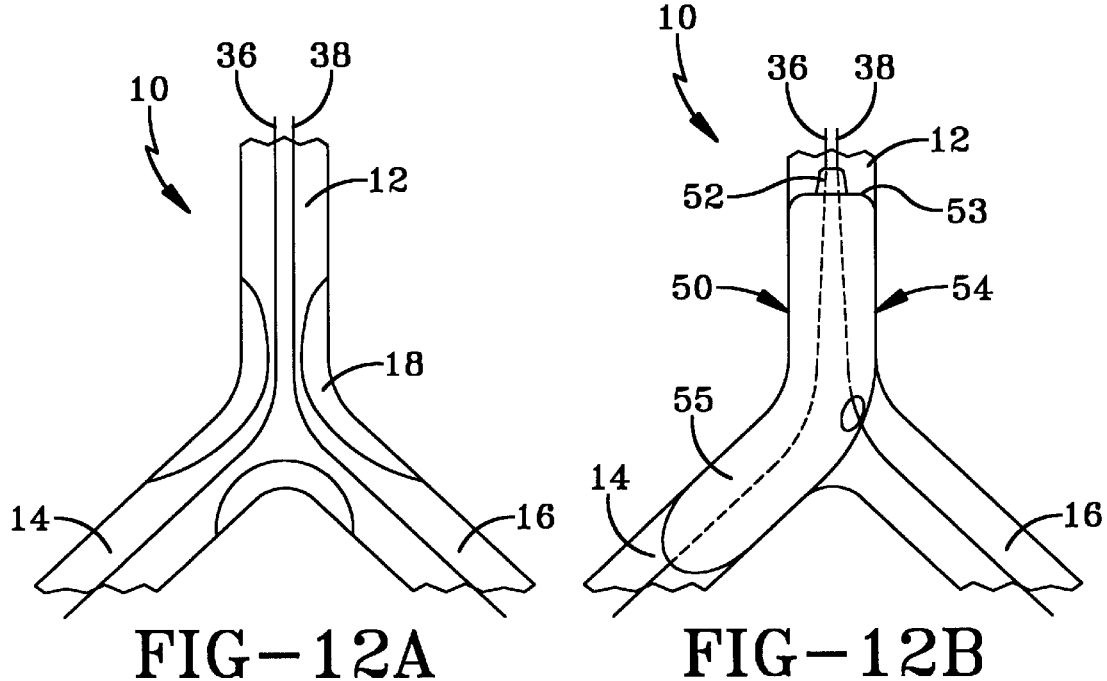
FIGS. 12A–12C illustrate dilation of a bifurcation lesion in accordance with one aspect of the present invention.
Figure 12C:
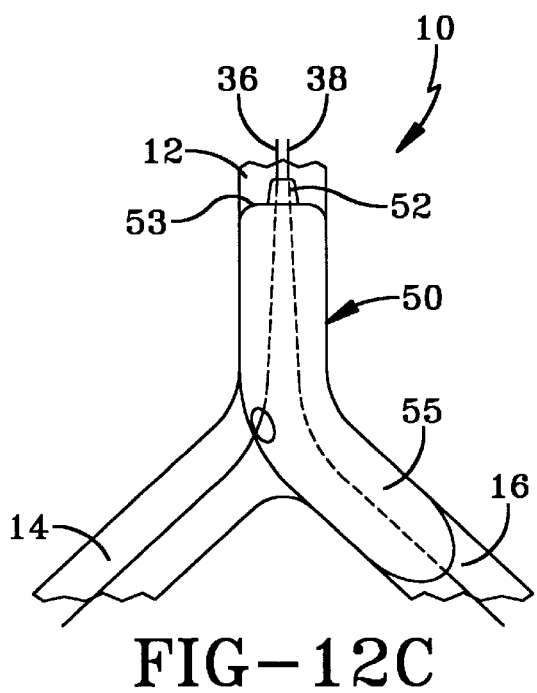

FIGS. 12A–12C illustrate dilatation in accordance with another aspect of the present invention. FIG. 12A illustrates that guidewires 36 and 38 are first placed in bifurcation 10 as described with respect to FIG. 5. Next, device 50 is loaded onto guidewires 36 and 38 (or it is preloaded onto the guidewires) such that guidewire 36 is disposed within lumen 58 and guidewire 38 is disposed within lumen 60. Device 50 is then advanced through the vasculature, with balloon 54 in the deflated position, until the distal end 55 of balloon 54 is within branch vessel 14, under the guidance of guidewire 36. Balloon 54 is then inflated, as shown in FIG. 12B, in order to perform dilatation of branch vessel 14 and parent vessel 12.

Device 50 is then withdrawn proximally and its orientation is switched such that guidewire 38 is disposed in guidewire lumen 58 and guidewire 36 is disposed within lumen 60. Again, device 50 is advanced through the vasculature with balloon 54 in the deflated position until the distal end 55 of balloon 54 is within branch vessel 16. Balloon 54 is then inflated, as illustrated in FIG. 12C, in order to dilate branch vessel 16 and parent vessel 12. It should, of course, be noted that balloon 54 can be inflated and deflated any desired number of times in order to accomplish dilatation.

Using this system, the guidewires 36 and 38 not only provide efficient placement of balloon 54 in the desired branch vessel, but the guidewires also help to maintain balloon 54 in place in bifurcation 10 during inflation. It should also be noted that device 64 as shown in FIG. 8B can be used in a similar manner to accomplish dilatation.

As can be seen, the present invention provides an improved system and technique for performing dilation and for deploying stents at bifurcation lesions. The present invention provides an apparatus with guidewire lumens configured to allow very convenient and accurate dilatation and placement of the stents, over two guidewires, without removing the guidewires from the vasculature, and without a great deal of excess manipulation required by the treating physician. Further, the present invention provides modified stent designs which allow quick and efficient placement of the stents in the vasculature, and which also conform closely to the geometry of the vasculature. This reduces the likelihood that either of the stents will impinge on the ostium of either of the branch vessels in the bifurcation. The present invention also provides a stent structure which is highly desirable for stenting a bifurcation lesion which only affects the parent vessel and one of the branch vessels. Aperture 82 allows circulation through the other branch vessel, without undue obstruction.

Although the present invention has been described with reference to preferred embodiments, workers skilled in the art will recognize that changes may be made in form and detail without departing from the spirit and scope of the invention.

What is claimed is:

1. A method of deploying a stent at a lesion site, the lesion site being located at a bifurcation in a parent vessel, the bifurcation bifurcating the parent vessel into first and second branch vessels, the method comprising:

advancing a first guidewire through the parent vessel into the first branch vessel;

advancing a second guidewire through the parent vessel into the second branch vessel;

configuring a first stent, having a distal end and a proximal end, with the first guidewire extending therethrough from the proximal end to the distal end thereof and with the second guidewire extending therethrough from the proximal end thereof to an aperture in the generally tubular wall structure;

advancing the first stent over the first and second guidewires until the distal end is disposed in the first branch vessel and the proximal end is disposed in the parent vessel;

deploying the first stent in the parent vessel and the first branch vessel, with the aperture disposed at an ostium of the second branch vessel;

advancing a second stent over the second guidewire through the proximal end of the first stent and through the aperture in the first stent and into the second brand vessel; and deploying the second stent in the second branch vessel.

2. The method of claim 1 wherein configuring the first stent comprises:

providing a stent deployment device including:
      an elongate member having a proximal end and a distal end and an inflation lumen extending therethrough; and
      an inflatable member disposed at a distal region of the elongate member, the inflatable member having a proximal end, a distal end and an intermediate portion therebetween and having an interior in fluid communication with the inflation lumen, the stent deployment device having a first guidewire lumen extending from the proximal end of the inflatable member to the distal end of the inflatable member and a second guidewire lumen extending from the proximal end of the inflatable member and having an ostium at the intermediate portion of the inflatable member.

3. The method of claim 2 wherein advancing the first stent comprises:

placing the first guidewire in the first guidewire lumen and the second guidewire in the second guidewire lumen.

4. The method of claim 2 wherein configuring the first stent comprises:

placing the first stent on an exterior surface of the inflatable member so the aperture in the first stent is generally aligned with the ostium of the second guidewire lumen such that the second guidewire exits the ostium of the second guidewire lumen and also exits the aperture in the first stent.

5. The method of claim 4 wherein deploying the first stent comprises:

inflating the inflatable member.

6. The method of claim 2 wherein advancing a second stent comprises:

providing the second stent having a proximal end and a distal end with a generally tubular wall extending therebetween, the proximal end being disposed at an angle such that the tubular wall has a long side and a short side in a longitudinal direction and such that the proximal end extends from the long side to the short side at an angle relative to a longitudinal axis of the second stent which is less than 90 degrees.

7. The method of claim 6 wherein advancing the second stent comprises:

arranging the second stent on the inflatable member distal of the ostium of the second guidewire lumen and angularly oriented on the inflatable member such that the long side of the proximal end is generally opposite the ostium of the second guidewire lumen.

8. The method of claim 7 wherein advancing the second stent comprises:

placing the second guidewire in the first guidewire lumen; and placing the first guidewire in the second guidewire lumen.

9. The method of claim 8 wherein deploying the second stent comprises:

arranging the second stent so the proximal end thereof is closely proximate the aperture in the first stent; and inflating the expandable member.

* * * * *

UNITED STATES PATENT AND TRADEMARK OFFICE
CERTIFICATE OF CORRECTION

PATENT NO.   : 6,096,073
DATED         : August 1, 2000
INVENTOR(S) : Mark Webster and H. Elizabeth Noll It is certified that error appears in the above-identified patent and that said Letters Patent is hereby corrected as shown below:

<u>Title page,</u>
Add Item [30], Foreign Application Priority Data as follows:
-- February 25, 1997 (NZ) New Zealand 314306 --.

Signed and Sealed this

Fourth Day of February, 2003

JAMES E. ROGAN
*Director of the United States Patent and Trademark Office*